US010458960B2

(12) United States Patent
Traidia et al.

(10) Patent No.: US 10,458,960 B2
(45) Date of Patent: Oct. 29, 2019

(54) INTEGRATED SYSTEM FOR QUANTITATIVE REAL-TIME MONITORING OF HYDROGEN-INDUCED CRACKING IN SIMULATED SOUR ENVIRONMENT

(71) Applicant: Saudi Arabian Oil Company, Dhahran (SA)

(72) Inventors: Abderrazak Traidia, Abqaiq (SA); Abdelmounam Sherik, Dhahran (SA); Arnold Lewis, Fresno, TX (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/207,906

(22) Filed: Dec. 3, 2018

(65) Prior Publication Data

US 2019/0113482 A1  Apr. 18, 2019

Related U.S. Application Data

(62) Division of application No. 14/989,630, filed on Jan. 6, 2016, now Pat. No. 10,295,508.

(51) Int. Cl.
*G01N 29/30* (2006.01)
*G01N 29/04* (2006.01)
(Continued)

(52) U.S. Cl.
CPC .......... *G01N 29/30* (2013.01); *G01N 17/006* (2013.01); *G01N 29/04* (2013.01); *G01N 29/043* (2013.01);
(Continued)

(58) Field of Classification Search
CPC ....... G01N 29/30; G01N 29/04; G01N 29/225
(Continued)

(56) References Cited

U.S. PATENT DOCUMENTS 4,721,536 A * 1/1988 Grob .................. C21D 9/50
148/520
5,351,203 A * 9/1994 Hoffman .............. G01B 15/025
378/15
(Continued)

FOREIGN PATENT DOCUMENTS

EP  0987536  3/2000
FR  2939510  6/2010

OTHER PUBLICATIONS

J. L. Gonzalez et al., Hydrogen-Induced Crack Growth Rate in Steel Plates Exposed to Sour Environments, CORROSION. 1997;53(12):935-943 (Year: 1997).*
(Continued)

*Primary Examiner* — Nathaniel T Woodward
(74) *Attorney, Agent, or Firm* — Leason Ellis LLP

(57) ABSTRACT

The present disclosure is directed to a method and system for monitoring hydrogen-induced cracking in at least one test specimen. The method includes the steps of: saturating a test solution with a gas comprising $H_2S$ and delivering the saturated test solution into a test cell, wherein the test cell comprises at least one specimen port and at least one test specimen. The specimen port is configured to receive the test specimen. The method also includes the step of exposing the at least one test specimen to the saturated test solution, wherein only one surface of each specimen is exposed to the saturated test solution and the step of scanning the test specimen with a ultrasonic transducer at two or more time points, wherein the ultrasonic transducer is operatively connected to the specimen port and configured to rotate completely around the symmetry axis of the test specimen to complete each scan.

17 Claims, 14 Drawing Sheets

(51) Int. Cl.
*G01N 29/22* (2006.01)
*G01N 17/00* (2006.01)

(52) U.S. Cl.
CPC ... *G01N 29/225* (2013.01); *G01N 2291/0234* (2013.01); *G01N 2291/0258* (2013.01); *G01N 2291/0289* (2013.01); *G01N 2291/101* (2013.01)

(58) Field of Classification Search
USPC .......................................................... 73/1.82
See application file for complete search history.

(56) References Cited

U.S. PATENT DOCUMENTS

| | | | | |
|---|---|---|---|---|
| 5,405,513 | A | * | 4/1995 | Lewis, II ............... G01N 17/00 204/404 |
| 7,021,143 | B2 | | 4/2006 | Dasch |
| 7,299,697 | B2 | | 11/2007 | Siddu et al. |
| 8,499,643 | B2 | | 8/2013 | Brown et al. |
| 8,513,020 | B2 | | 8/2013 | Hehn et al. |
| 9,212,986 | B2 | * | 12/2015 | Zhang .................... G01N 27/02 |
| 9,726,594 | B2 | * | 8/2017 | Jovancicevic ......... G01N 17/02 |
| 2006/0219011 | A1 | * | 10/2006 | Siddu ................. G01N 29/0645 73/597 |
| 2010/0032048 | A1 | * | 2/2010 | Yokoyama .............. C22C 38/02 138/171 |
| 2011/0100131 | A1 | | 5/2011 | Brown et al. |
| 2014/0283612 | A1 | | 9/2014 | Williams et al. |

OTHER PUBLICATIONS

V. Smanio et al., "Acoustic Emission Monitoring of Wet $H_2S$ Cracking of Linepipe Steels: Application to Hydrogen-Induced Cracking and Stress-Oriented Hydrogen-Induced Cracking", CORRISION Journal 67:6, Jun. 2011.

J. Kittel et al., "Hydrogen induced cracking (HIC) testing of low alloy steel in sour environment: Impact of time of exposure on the extent of damage", Corrosion Science 52, (2010). Available online Dec. 5, 2009.

JL. Gonzalez et al, "Hydrogen-Induced Crack Growth Rate in Steel Plates Exposed to Sour Environments", Corrosion Journal 53:12, (Dec. 1997).

Traidia, A.M. El-Sherik, and H. Attar (2015) Recommended Specimen Dimensions and Boundary Conditions for Measurement of Hydrogen Permeation in Thick Carbon Steel Plates. Corrosion: May 2015, vol. 71, No. 5, pp. 585-597.

RC. Brouwer et al., "Modelling Hydrogen Induced Crack Growth: Validation by Comparison with Experiment", Oct. 1, 1995, Corrosion 95, Paper No. 70.

* cited by examiner

FIG. 3
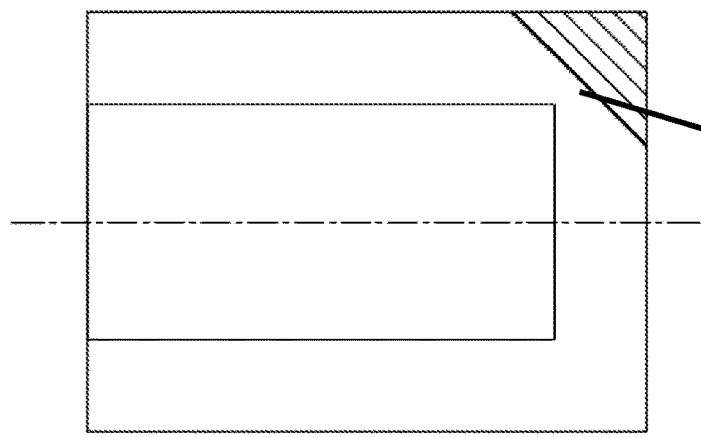
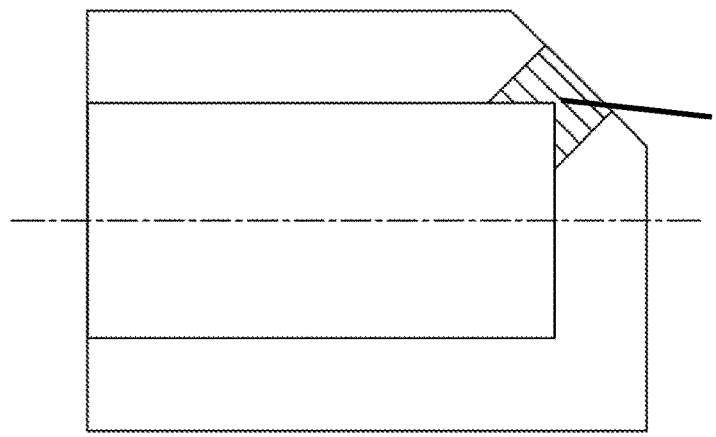
304
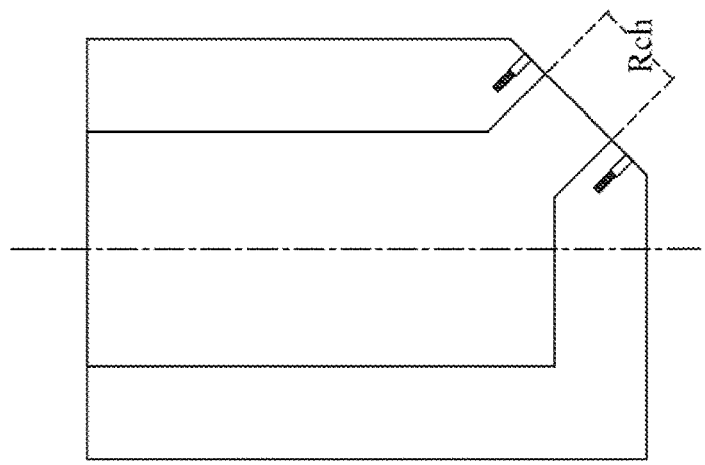
302

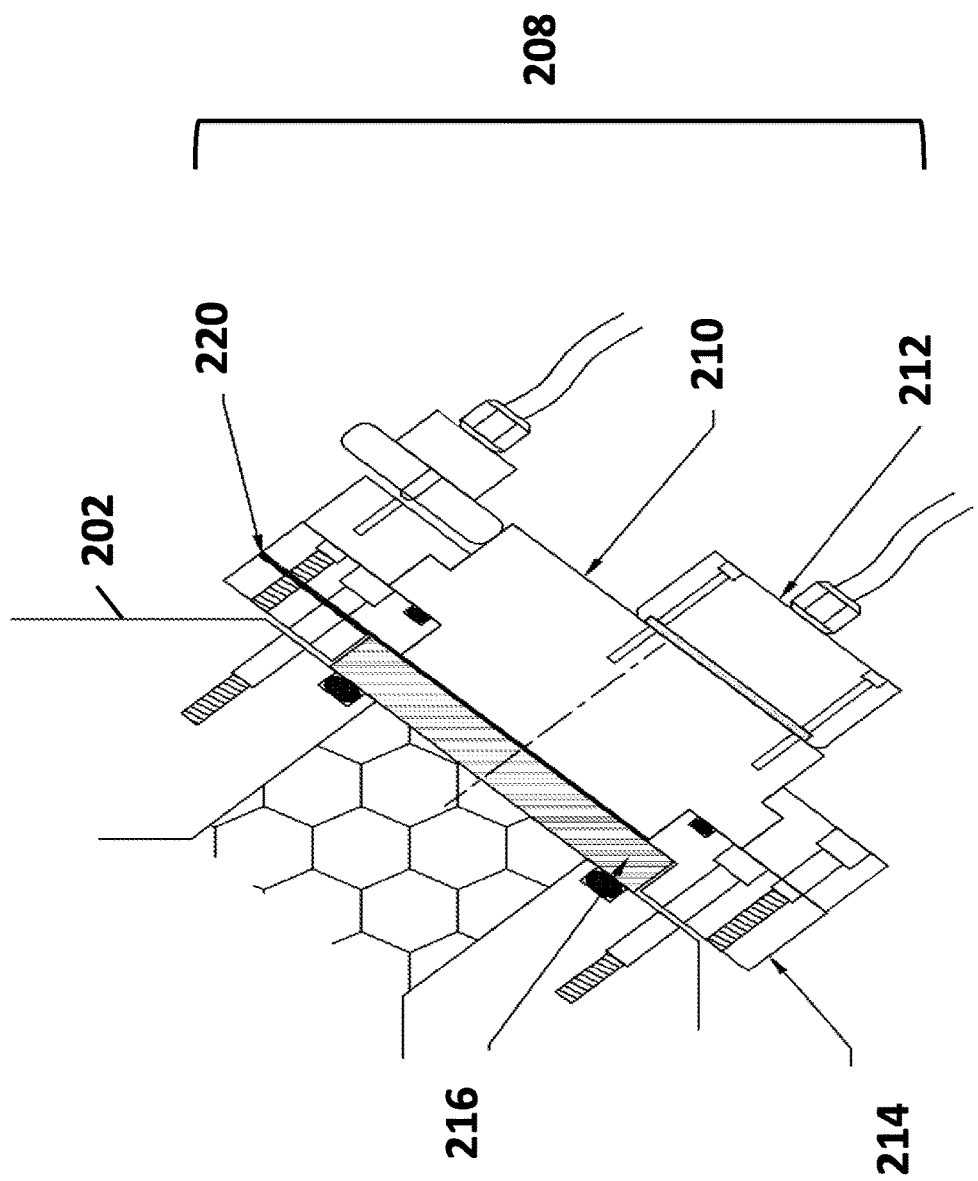

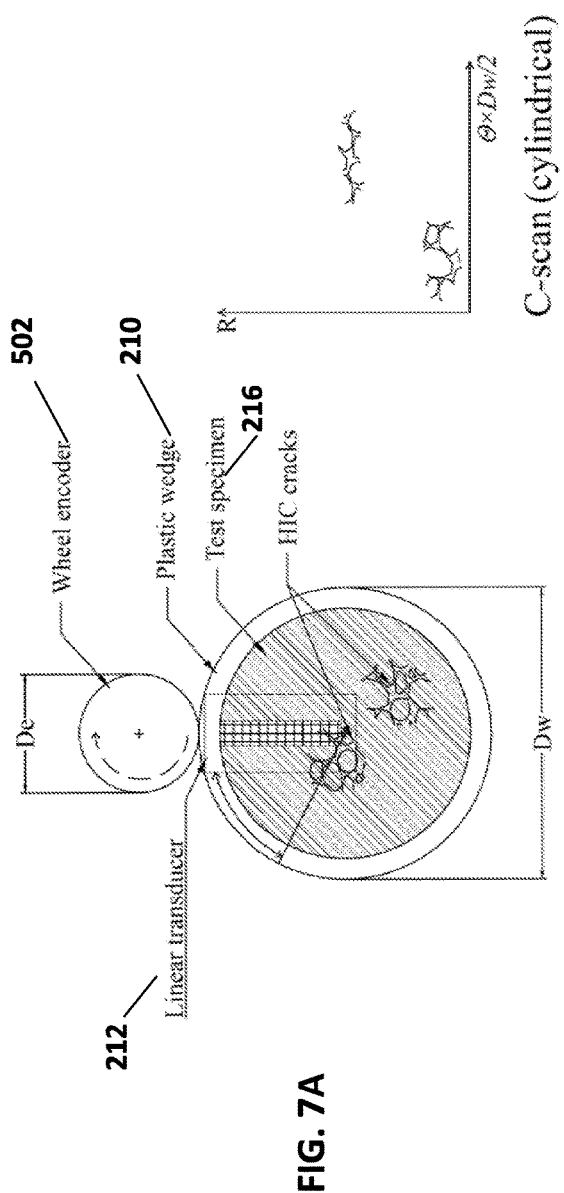
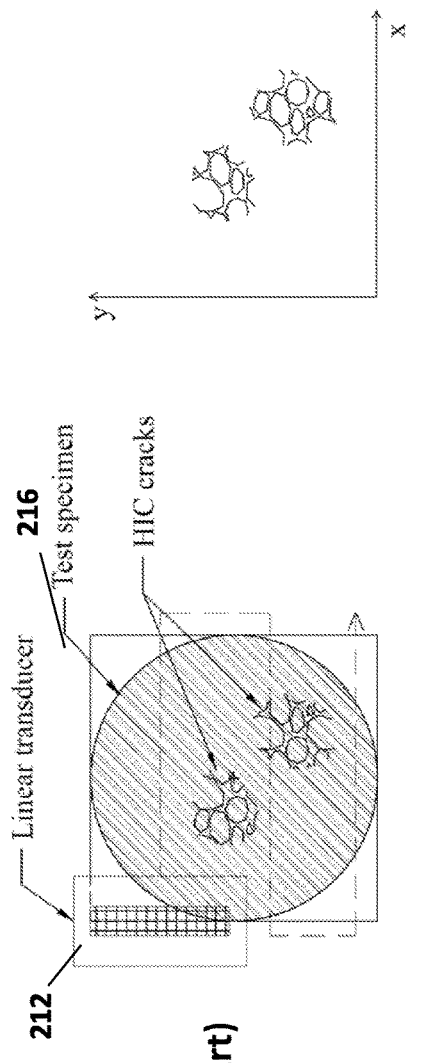
FIG. 7A
FIG. 7B
(Prior Art)

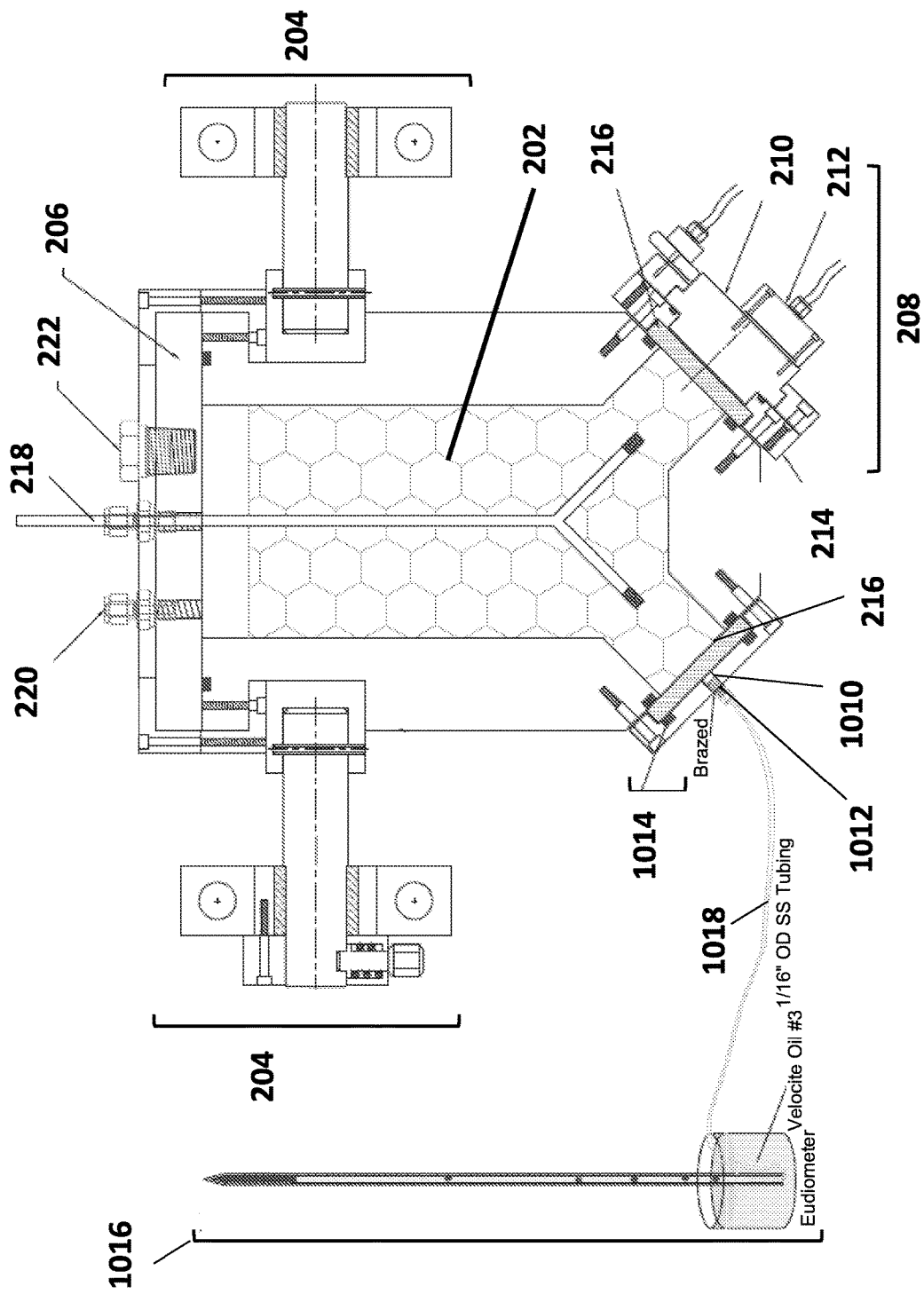

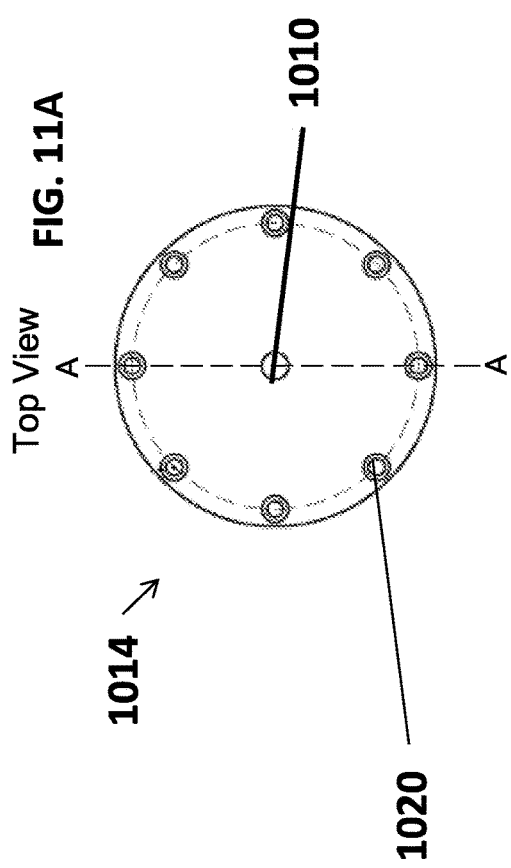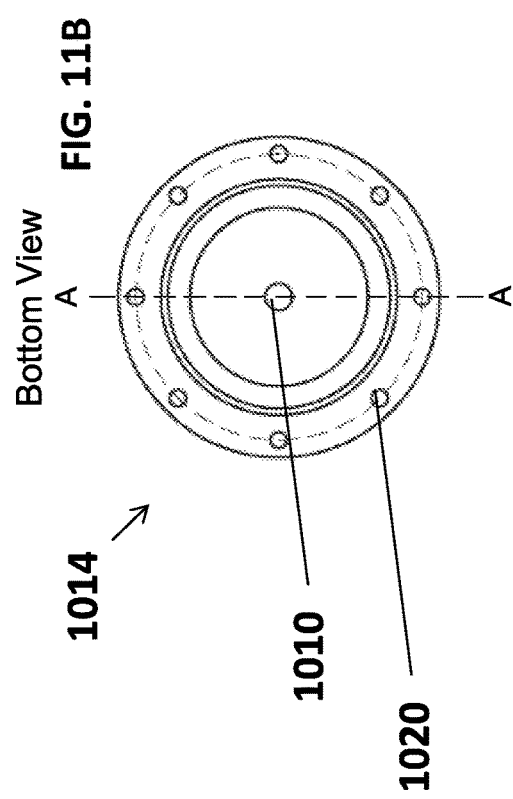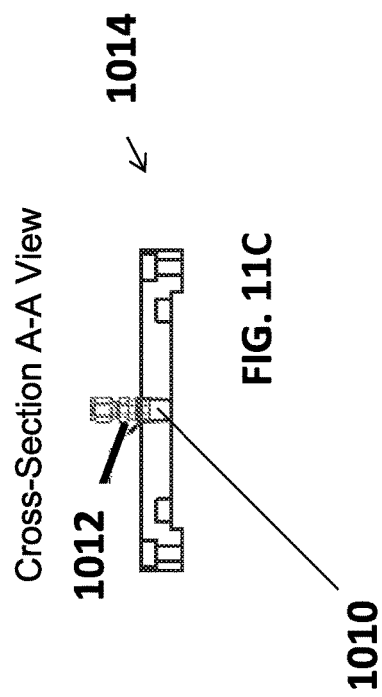

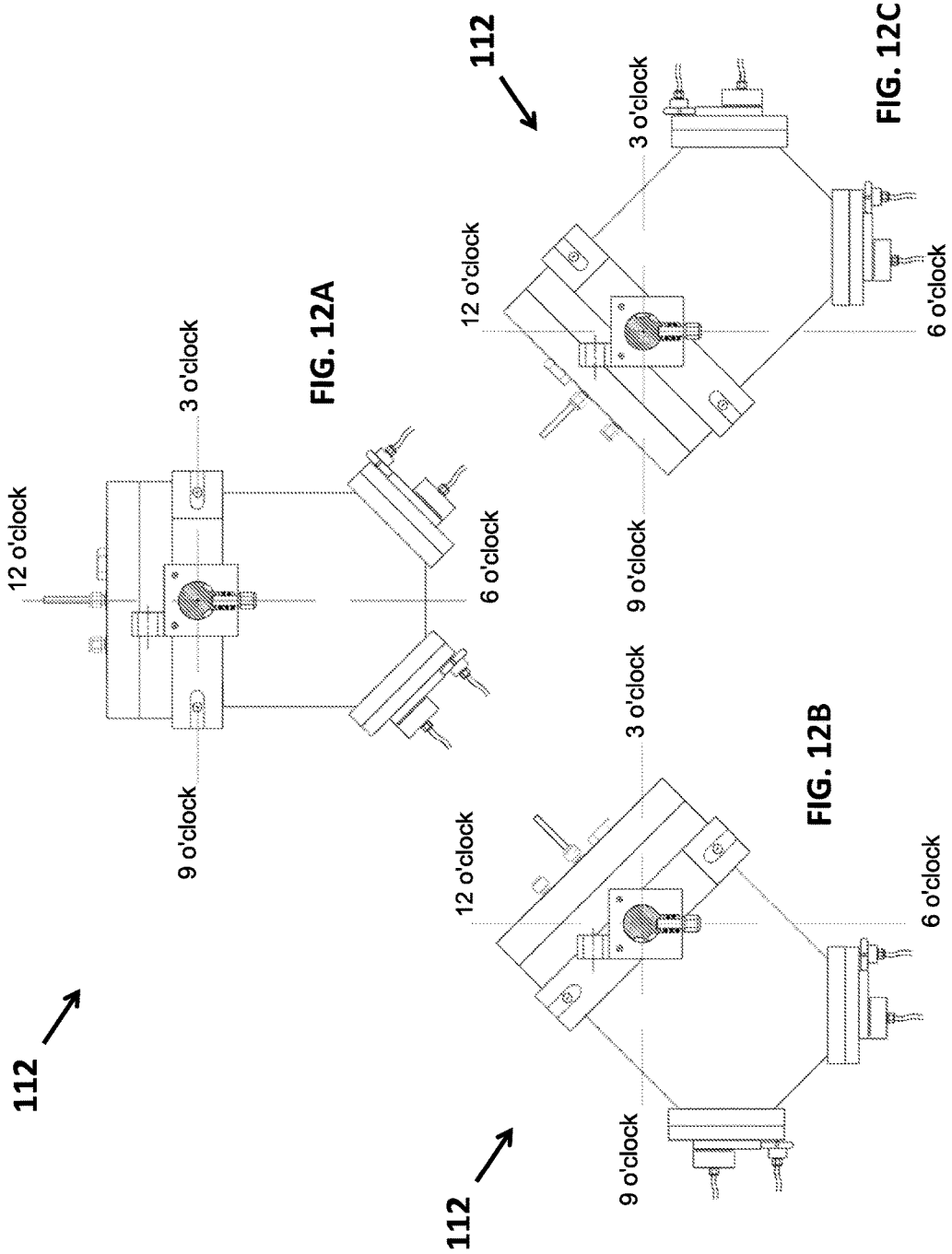

INTEGRATED SYSTEM FOR QUANTITATIVE REAL-TIME MONITORING OF HYDROGEN-INDUCED CRACKING IN SIMULATED SOUR ENVIRONMENT

CROSS-REFERENCE TO RELATED PATENT APPLICATIONS

This application is a divisional of U.S. Non-Provisional application Ser. No. 14/989,630, filed Jan. 6, 2016, the entire contents of which is incorporated by reference herein as if expressly set forth in its respective entirety herein.

FIELD OF THE INVENTION

The present invention relates to a system and process for quantitative monitoring of the initiation and growth of hydrogen-induced cracking damage in steel and more particularly, relates to laboratory simulations of sour service conditions in order to predict and track the initiation and growth of HIC damage in sour service equipment.

BACKGROUND

Hydrogen-induced cracking (HIC) can be a major problem for pipelines and pressure vessels, specifically those that service wet sour conditions, i.e., operate in a wet $H_2S$-containing environment. In general, HIC is a bulk type of cracking in metallic structures (e.g., steel), such as pipelines, piping systems and pressure vessels, that can occur as a result of atomic hydrogen being dissolved in the metal. In particular, hydrogen atoms, which are either produced (1) as a result of the corrosion reaction between $H_2S$ and iron taking place at the metal surface, or (2) by poor cathodic protection (overprotection), can diffuse through interstitial sites in the metal, and recombine to form high-pressure hydrogen gas within the metal imperfections. The increased pressure of the hydrogen gas within the metal defects then causes cracks or blisters to form and grow in the bulk metal, which can subsequently link to each other in a stepwise manner and may lead to the structural failure of the metallic structure. Structural failure within sour service pressure equipment can results in safety and environmental hazards due to the potential leaking of sour gas. As such, the ability to predict and track the initiation and growth of HIC in sour service equipment is of the utmost importance.

Currently, sour service operations regularly monitor the equipment for signs of HIC, and when HIC is discovered, the affected locations are inspected even more frequently to determine whether pressure de-rating is required and ultimately when replacement equipment is needed. For example, for sour service systems, all vessels with linear HIC damage can be monitored by advanced ultrasonic testing on a regular interval (e.g., a yearly basis), while vessels showing step-wise cracking damage (a more severe form of HIC) can be monitored more frequently (e.g., semi-annually). This frequent monitoring, however, is costly and time-consuming. For a given metal grade (e.g., steel grade), knowledge of the HIC growth rate and its relationship with the operating conditions (e.g., temperature, pressure, pH, percentage of $H_2S$) would allow for greater efficiency in the monitoring of HIC-damaged vessels. In particular, with a greater understanding of the factors controlling the growth rates of HIC, monitoring could be limited to those vessels at the highest risk of failure, rather than monitoring all HIC-damaged equipment on a systematic basis. In other words, the monitoring procedures could move from a schedule-based inspection (SBI) system to a risk-based inspection (RBI) system. As such, there is a need for reliable ways to predict the initiation and quantify the growth rate of HIC damage in metallic structures operating in a sour service environment in order to enhance the efficiency of equipment monitoring procedures.

SUMMARY

The present disclosure is directed to a method and system for quantitative monitoring of hydrogen-induced cracking in at least one test specimen. The method includes the steps of: saturating a test solution with a gas comprising $H_2S$ and delivering the saturated test solution into a test cell, wherein the test cell comprises at least one specimen port and at least one test specimen. The specimen port is configured to receive the test specimen. The method also includes the step of exposing the at least one test specimen to the saturated test solution, wherein only one surface of each specimen is exposed to the saturated test solution and the step of scanning the test specimen with an ultrasonic transducer at two or more time points, wherein the ultrasonic transducer is operatively connected to the specimen port and configured to rotate completely around the symmetry axis of the test specimen to complete each scan.

The system for monitoring hydrogen-induced cracking in a laboratory environment includes a source of sour gas and a test solution tank comprising a test solution and into which the sour gas is introduced such that the test solution becomes saturated with the sour gas. A test cell is provided and defines a semi-open fluid vessel which is able to hold at least one test specimen and in which the sour corrosion reaction will take place. The fluid vessel is in fluid communication with the test solution tank such that the fluid vessel receives the saturated test solution, through pressure differential. A test cell holder is configured to rotate the test cell, at three different positions, such that one surface of each test specimen is exposed to the saturated test solution. The system includes an ultrasonic transducer that is operatively connected to at least one specimen port and is configured to rotate around the test specimen to periodically scan the HIC defects present in the bulk material.

BRIEF DESCRIPTION OF THE DRAWINGS

Further aspects of the present disclosure will be more readily appreciated upon review of the detailed description of its various embodiments, described below, when taken in conjunction with the accompanying drawings, of which:

FIG. 3 is a schematic of a test cell illustrating the creation of a specimen port on the bottom portion of the test cell in accordance with one or more embodiments of the present application;

FIG. 6 is a schematic of the specimen port and its components in accordance with one or more embodiments of the present application;

FIGS. 7A-B are C-scan displays of longitudinal bulk HIC cracks located in a test specimen in accordance with one or more embodiments of the present application. FIG. 7A also displays the rotation of the transducer with respect to the specimen axis in conjunction with the use of a wheel encoder. FIG. 7B displays conventional movements of the probe in the Cartesian (x, y) directions;

FIG. 10 is a schematic of an alternative embodiment of the test cell and its components in accordance with one or more embodiments of the present application;

FIGS. 11A-C are schematics of the hydrogen permeation specimen clamp and its components in accordance with one or more embodiments of the present application;

FIGS. 12A-C are schematics of the different orientations of the test cell and test specimens in accordance with one or more embodiments of the present application;

DETAILED DESCRIPTION CERTAIN OF EMBODIMENTS OF THE INVENTION

Figure 1:
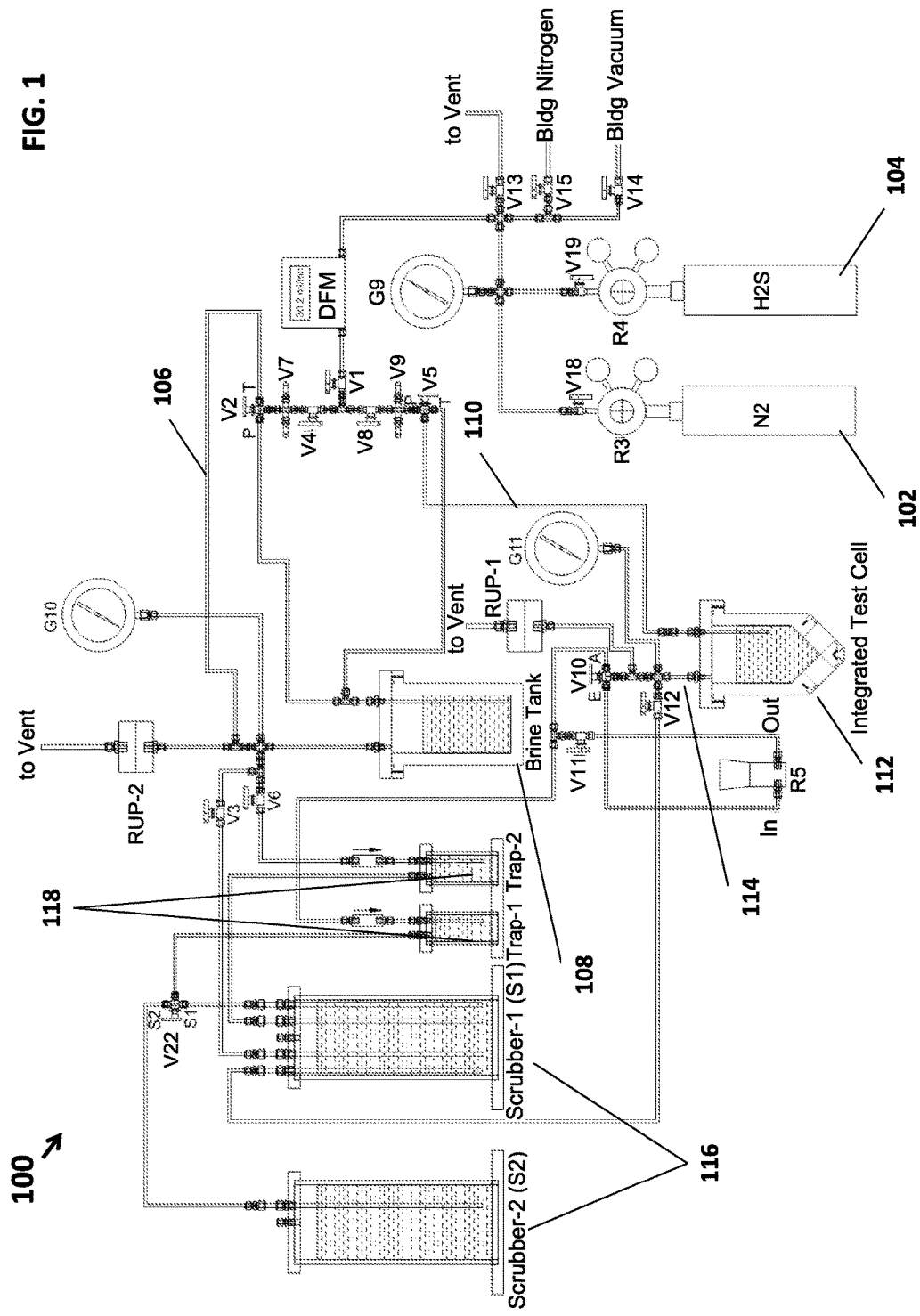
FIG. 1 is a schematic of a system for quantitative monitoring HIC in one or more test specimens in a sour environment in accordance with one or more embodiments of the present application.

The present disclosure details systems and methods for the quantitative monitoring of HIC in a laboratory environment or the like that simulates a sour service environment. In particular, the present application is directed to a system, as described herein, that is remote from the sour service environment but simulates conditions thereat. More specifically, the systems of the present application can monitor the initiation and growth of HIC damage in test specimens, thereby simulating the initiation and growth of HIC damage in actual sour service pipeline operations. The systems can accurately track the initiation, growth (e.g., size, shape, location), and determine the growth rate (in unit of crack size per unit of time) of HIC in the test specimens in a given sour environment, which will allow field operators to better predict the growth rate of active HIC damage in portions of actual sour service assets (e.g., pipelines, plant vessels, piping systems). The system can also be used to detect the presence of step-wise cracking (SWC) in the test specimens.

In the methods of the present application, the test specimens are made from the same material as the sour service equipment of interest (e.g., pipelines, plant vessels) and have a substantially similar thickness in order to provide conditions that allow the prediction and tracking of the initiation and growth of HIC in actual sour service equipment. The test specimens can comprise any material that is susceptible to hydrogen embrittlement or HIC damage. For instance, in one or more embodiments, the test specimens are comprised of a metal, such as steel. The one or more test specimens are held in one or more specimen ports (one test specimen per one specimen port) within a test cell where they are exposed to the test solution. The test solution is comprised of water, as well as salts or organic acids to simulate produced water in an oilfield. The test solution can also contain additional elements, including but not limited to oils, gases, and acids. Further, the test solution is pre-saturated with a test gas that can be pure $H_2S$ or a mixture of $H_2S$ and other gases (with known $H_2S$ partial pressure in the mixture). During operation, at a certain pressure and temperature, the test gas used to saturate the test solution is continuously bubbled into the test cell at a fixed flow rate. Only one surface of each test specimen is in contact with the saturated test solution throughout the test duration, thereby simulating the exposure of actual field equipment to the sour environment. For example, in a pipeline in the field, the inner surface of the pipe is exposed to the fluid flowing therethrough, while the outside surface is open to the air, therefore creating a continuous driving force for hydrogen to diffuse from the inner surface to the outer wall. The continuous bubbling of the saturated test solution promotes the absorption of the produced hydrogen (as a result of corrosion) into the exposed surface of the test specimen, which eventually leads to HIC damage within the bulk material.

The HIC damage within the test specimen is then monitored in real time by a rotating ultrasonic transducer attached to the specimen port. The rotating ultrasonic transducer can provide a full three-dimensional ultrasonic tomography of the test specimen at different time points during the test duration at a frequency than can be designated by the operator of the test. A subsequent analysis of the tomographic data at the different time points can then be used to derive the initiation, growth (e.g., size, shape, location), and growth rate for each individual HIC defect in the test specimen, and can also be used to quantify the probability of through-thickness coalescence of the individual HICs into Step-Wise Cracking (SWC).

The referenced systems and methods for the monitoring of HIC in a laboratory environment are now described more fully with reference to the accompanying drawings, in which one or more illustrated embodiments and/or arrangements of the systems and methods are shown. The systems and methods are not limited in any way to the illustrated embodiments and/or arrangements as the illustrated embodiments and/or arrangements described below are merely exemplary of the systems and methods, which can be embodied in various forms, as appreciated by one skilled in the art. Therefore, it is to be understood that any structural and functional details disclosed herein are not to be interpreted as limiting the systems and methods, but rather are provided as a representative embodiment and/or arrangement for teaching one skilled in the art one or more ways to implement the systems and methods.

FIG. 1 illustrates an exemplary system for monitoring HIC defects in one or more test specimens in laboratory environment. FIG. 1 also shows an exemplary flow scheme. The system 100 includes a nitrogen ($N_2$) gas vessel (tank or container) 102 and a test gas (e.g., hydrogen sulfide [$H_2S$]) vessel (tank or container) 104. In certain embodiments, prior to the test run, the tubing connecting vessels 102 and 104 to the rest of the system (e.g., conduit 106) can be vacuumed for approximately 10 minutes to remove any trace of oxygen. Then, in one or more embodiments, N₂ gas can be released from the vessel 102 to purge the rest of system 100 of any oxygen. In certain embodiments, the minimum flow rate of the N₂ gas through the system can be 100 mL/min and the N₂ gas can purge the system for a minimum of 24 hours. In embodiments in which N₂ gas is used to purge the system, following the purge, the N₂ gas flow is shut off. In one or more embodiments, N₂ gas from vessel 102 can also be used to purge the system following each test run. A main advantage of removing oxygen from the system is to better reproduce oilfield conditions, as very few oilfield H₂S environments contain oxygen. The removal of oxygen from the system is important as oxygen could react with H₂S to form elemental sulfur, which can block the fluid conduits. On the other hand, in alternative embodiments, the system can contain oxygen to simulate certain abnormal conditions, if required.

In general, the fluids (gases and liquids) of the system 100 flow between containers in the system through fluid conduits. These fluid conduits can be made of one or more corrosive-resistant alloys.

In one or more embodiments, the flow rate of the fluids of system 100 is controlled by a flow control system that includes one or more digital mass flow meters, pressure regulators, valves, gauges, and/or pressure safety elements (e.g., rupture disks). While the flow control system of system 100 (see, FIG. 1) described below is configured in a particular way, any number of configurations for the valves, regulators, gauges and the like can be used for the flow control system in order to accomplish the specified flow rates of fluids within the system 100.

With continued reference to FIG. 1, during the step of vacuuming conduit 106 (described above), valves V14, V18, and V19 are opened, while valves V1, V13, and V15 are closed. Similarly, during the step of purging the system 100 with N₂ (as described above), valves V3, V11, V12, V14, and V19 are then closed, valves V4, V6, and V8 are opened, three-way valves V2 and V5 are put in the purge ("P") position), V10 is put in the ambient ("A") position and regulators V7 and V9 are half-opened. Additionally, for the N₂ purging step, the main valve (V18) of vessel 102 is opened and the pressure reading on gauge G9 is regulated to an ambient positive pressure (less than 10 psig) using regulator R3.

In one or more embodiments, in preparation for each test run, a minimum volume ($V_{min}$) of the test solution can be prepared, and the pH and water of the test solution can be adjusted to the desired levels. The preparation of the $V_{min}$ allows the experimenter to maximize the ratio of test solution volume to the total exposed test specimen surface S ($2 \times \pi R_{ch}^2$), which helps to ensure that the pH of the test solution remains constant during the entire test duration. In one or more embodiments, a value of ($V_{min}$/nS)=30 can be used, where n is the number of test specimens used in the experiment. After preparation, the test solution is then placed in a test solution tank (brine tank) 108 to be purged with nitrogen and then saturated with the desired test gas (e.g., sour gas mixture), before being transferred to the test cell 112 (the fluid vessel of the test cell 112), as discussed in greater detail below. The test solution is transferred to a separate tank (test solution tank 108) for the purging/saturation stage before entering the test cell 112 in order to prevent contamination or corrosion of the test specimen(s) during the purging/saturation stage. Indeed, having the test specimen(s) in a separate and dry cell (the test cell 112) during this stage ensures they will not start corroding early which would create false corrosion surfaces and affect the measurements. Further the ability to transfer the purged test solution from the test solution tank 108 into the test cell 112 without exposure to air provides an advantage over conventional methods.

As mentioned above, following preparation of the test solution, the system is purged with nitrogen (N₂). After complete purging of the system with N₂, the test gas is released from vessel 104 to begin the test run. The test gas flows from vessel 104 through fluid conduit 106 and into a test solution tank 108, which contains the test solution. In the embodiment shown in FIG. 1, the flow of test gas from vessel 104 to tank 108 is accomplished by closing valve V18 (N₂ gas valve), and opening V19 and the main valve of vessel 104. Further, regulator R4 is also slowly opened to maintain a constant pressure in the system, which can be read in gauge G9. The gas flow rate is controlled via the regulators V7 and V9, and if needed by a slight increase in regulator R4. In one or more embodiments, the gas flow rate of the digital flow meters (DFM) should be a minimum of 150 ml/mn.

In one or more embodiments, the test gas is a mixture of gas that contains a known partial pressure of H₂S. Upon entering the test solution tank 108, the test gas saturates the test solution. In one or more implementations, the test gas is pumped into the test solution tank 108 for a minimum of two hours to ensure complete saturation of the test solution, at which point the flow rate of the test gas is reduced via regulators V7 and V9. For example, the flow rate of the test gas can be reduced to a default level of 30 ml/min to reasonably ensure continuous H₂S saturation of the test solution during the duration of the test run.

In one or more embodiments, prior to saturation of the test solution, the test gas should be stored in vessel 104 with maximum pressure. The partial pressure of the dissolve gases is an important parameter to be considered in preparing of the test gas. As such, in preparing the test gas, the following relationship between H₂S gas and pressure can be used: $xH_2S^{test} \times p^{test} = xH_2S^{field} \times p^{field}$. $xH_2S^{test}$ and $xH_2S^{field}$ denote the mole fraction of H₂S in the gas mixture for the test run and the actual field conditions, respectively, while $p^{test}$ and $p^{field}$ denote the test pressure and the equipment operating pressure in the actual field conditions, respectively.

With continued reference to FIG. 1, following saturation of the test solution, the saturated test solution is then transferred from tank 108 via fluid conduit 110 to the test cell 112. More specifically, the saturated test solution is transferred from the test solution tank 108 to the test cell 112 using the test gas flow itself as a way of lifting the solution. To accomplish this, three-way valves V2 and V5 are turned to the transfer ("T") position. In certain embodiments, the fluid conduit 110 can be transparent to allow for visual monitoring of the test solution transfer, and in particular, to determine when the test solution transfer has ended. After the saturated test solution has been transferred from the test solution tank 108 to the test cell 112, the testing of one or more test specimens in the test cell 112 can be initiated.

In embodiments in which the test run is performed at ambient pressure, once the test solution has been transferred to the test cell, three-way valves V2 and V5 are switched to the "purge" position ("P" position), while valve V4 and regulator V7 are fully closed. Further, valve V11 is kept on in an ambient ("A") position and V9 can be adjusted to set the desired gas flow rate.

Similarly, in embodiments in which the test run is performed at an elevated pressure, after the test solution has been transferred to the test cell, three-way valves V2 and V5 are switched to the purge ("P") position, while valve V4 and regulator V7 are fully closed. However, valve V10 must also be switched to an elevated position ("E" position), and valve V11 must be opened. Further, regulator V9 must be adjusted to set the desired gas flow rate value. In parallel, regulator R5 (and if needed R4) can also be used to adjust the test cell pressure in gauge G11 to the desired test pressure value. It is important to note that the test pressure cannot exceed the maximum operating pressure of the test cell. For example, in one or more embodiments, the safety rupture disks (RUP-1 and RUP-2) can rupture if the test pressure exceeds the maximum operating pressure of the test cell.

Figure 2:
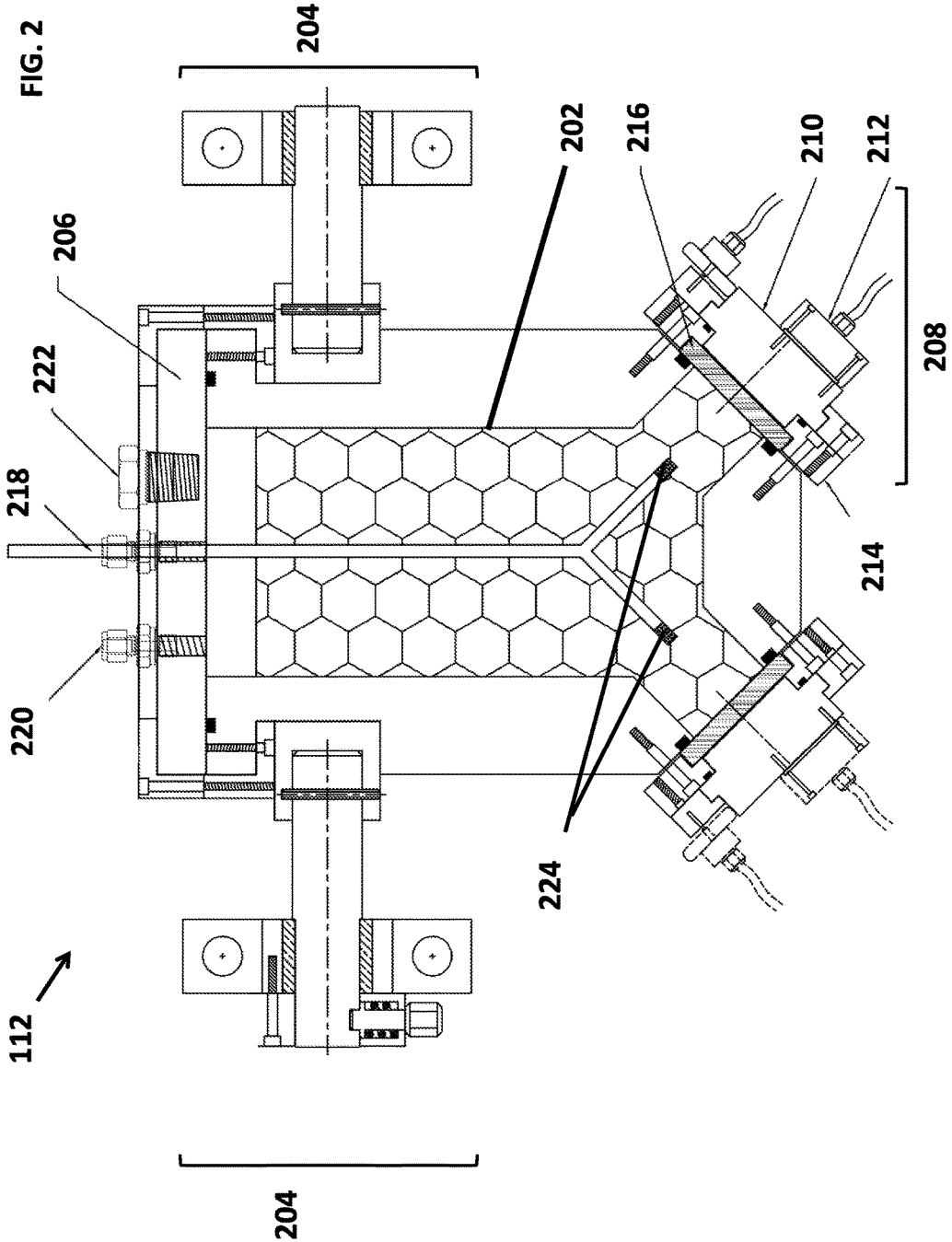
FIG. 2 is a schematic of a test cell and its components in accordance with one or more embodiments of the present application.

A schematic of the test cell 112 and its components in accordance with one or more embodiments is shown in FIG. 2. With reference to FIG. 2, the test cell 112 can comprise a semi-open fluid vessel 202, which contains the saturated test solution. In one or more implementations, the semi-open fluid vessel 202 can be made of any corrosion and/or chemical resistant material as known to those of ordinary skill in the art. Preferably, the material of the semi-open fluid vessel 202 can also have suitable thermomechanical properties and resistance to $H_2S$ permeation. For example, semi-open fluid vessel can be made of polyvinylidene fluoride (PVDF). The test cell 112 can also comprise a rotating test cell holder 204, which holds the test cell 112 to the control panel (e.g., a metallic stand on which the system components, apart from the gas cylinders, are fixed [not shown]), and can rotate the test cell 112 itself. In certain implementations, the rotating test cell holder 204 can rotate and lock the test cell 112 at 0 degrees, +45 degrees and −45 degrees with respect to the gravity direction. In certain implementations, the test cell 112 can be rotated and fixed in any position between and including −45 degrees and +45 degrees. The test cell 112 can further comprise a top cover 206 and at least one specimen port 208, which can comprise a wedge 210, a ultrasonic transducer 212, an encoder (not shown, see FIG. 7A [wheel encoder 502]), and a clamp 214, and a test specimen 216.

With continued reference to FIG. 2, the top cover 206 of the test cell 112 can include at least two openings: a first opening 218 for receiving fluid conduit 110 for the inflow of the test gas and a second opening 220 for receiving fluid conduit 114 for outputting the test gas to one or more scrubber tanks 116 (as shown in FIG. 1) at the end of the test run. In one or more implementations, screens 224 can be installed at the end of fluid conduit 110 that terminates within the semi-open fluid vessel 202 to allow for optimal diffusion and bubbling of the saturated test gas and to ensure agitation of the test solution around the test specimen. The screens 224 can also help to ensure a homogeneous pH in the area around the test specimen. In at least one implementation, the top cover 206 can contain a third opening 222 for: (1) the use of other intrusive measurement devices including but not limited to a Linear Polarization Resistance (LPR) probe for general corrosion monitoring, an in-situ pH measurement probe, or an in-situ temperature sensor; (2) the introduction of pH-adjusting chemicals (such as NaOH or HCl), or the injection of corrosion inhibitors, with the aim to assess their performance on reducing corrosion and hydrogen embrittlement (through reduction of the hydrogen permeation rate); and (3) the use of an auxiliary electrode, electrically wired to the test specimen through an external potentiostat, in order to simulate a Cathodic Protection (CP). Thus, in at least one implementation, the system of the present application is flexible in that it is capable of charging the specimen with hydrogen though (a) $H_2S$ corrosion only, (b) through CP (in this case the test solution in the test solution tank does not need to be pre-saturated with $H_2S$) or (c) through a combination of both. The latter can accelerate the HIC phenomena, which can simulate long term aging of sour service equipment. In one or more implementations, the top cover 206 can be made of polyetheretherketone (PEEK).

As mentioned above, the test cell can also comprise at least one specimen port integrated into the test cell. In one or more embodiments, the specimen port(s) are fashioned on the bottom end of the test cell. For instance, as illustrated in FIG. 3, to create a specimen port in the test cell, a plane 302 is first created at the bottom end side (closed side) of the test cell (e.g., at an angle of approximately 45°). Next, a through-thickness hole 304 centered in the plane is drilled to create the specimen port. In one or more embodiments, the radius of the drilled hole ($R_{ch}$), corresponds to the radius of the corrosion surface where exposure of the saturated test solution to the test specimen will take place. Depending on the dimensions of the test cell, several specimen ports can be created at the bottom end of the test cell.

In one or more embodiments, as shown in FIG. 2, the test cell 112 can comprise at least one specimen port 208. The specimen port 208 can comprise several components, including a wedge 210, an encoder (not shown, see FIG. 7A [wheel encoder 502]), an ultrasonic transducer 212, and two clamps 214. In one or more embodiments, the ultrasonic transducer 212 is fixed to the top of the wedge 210. The two clamps 214 are used to hold the sides of the test specimen 216. The front and back surfaces of the test specimen 216 are held between the wedge 210 and the edges test cell 112 itself. In one or more embodiments, the test specimen 216 can be fixed onto the test cell 112 via clamps 214 using screws. The top portion of the wedge 210 is also held between the clamps 214. In particular, the wedge 210 is held between two clamps 214 with a fitting clearance to allow for the 360° rotation of the wedge 210 with respect to the symmetry (vertical) axis (as shown by the dashed line) of the test specimen 216. In one or more implementations, the wedge 210 can be cylindrical in shape.

The test specimens 216 can be manufactured in any number of ways know to those of ordinary skill in the art. In one or more implementations, the one or more test specimens can be machined from a steel plate (or pipe) used to manufacture the sour service equipment of interest. The test specimen diameter shall be in agreement with the specifications of the test cell, in particular the machining dimensions of the test specimen port. In a preferred embodiment, the test specimen is of maximum thickness, which is limited by the curvature of the starting material (e.g., plate, pipe) from which it is made. For example, if the curvature of the starting material is zero, i.e., a flat plate, the test specimen thickness is the thickness of the plate.

Figure 4:
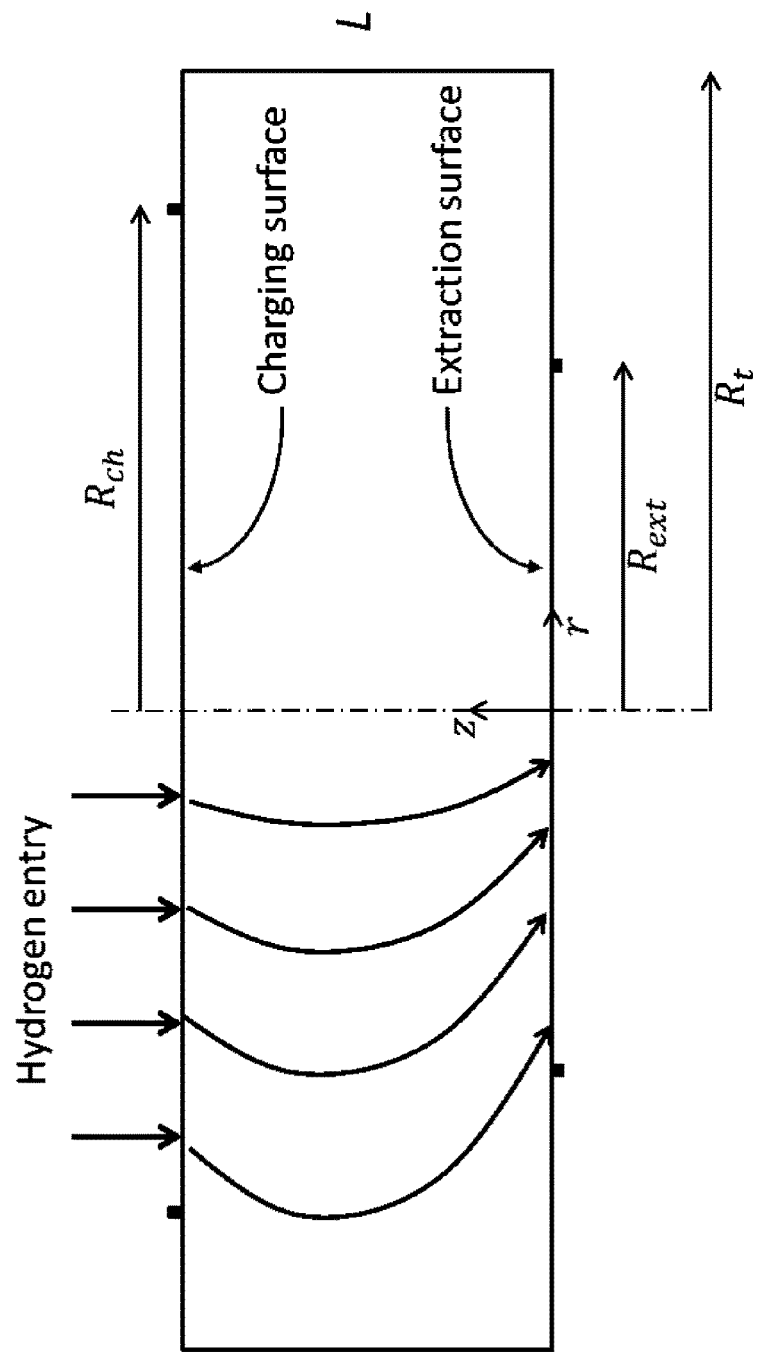
FIG. 4 is a diagram illustrating the dimensions of a test specimen and the absorption of hydrogen at the surface of the test specimen in accordance with one or more embodiments of the present application.
Figure 5:
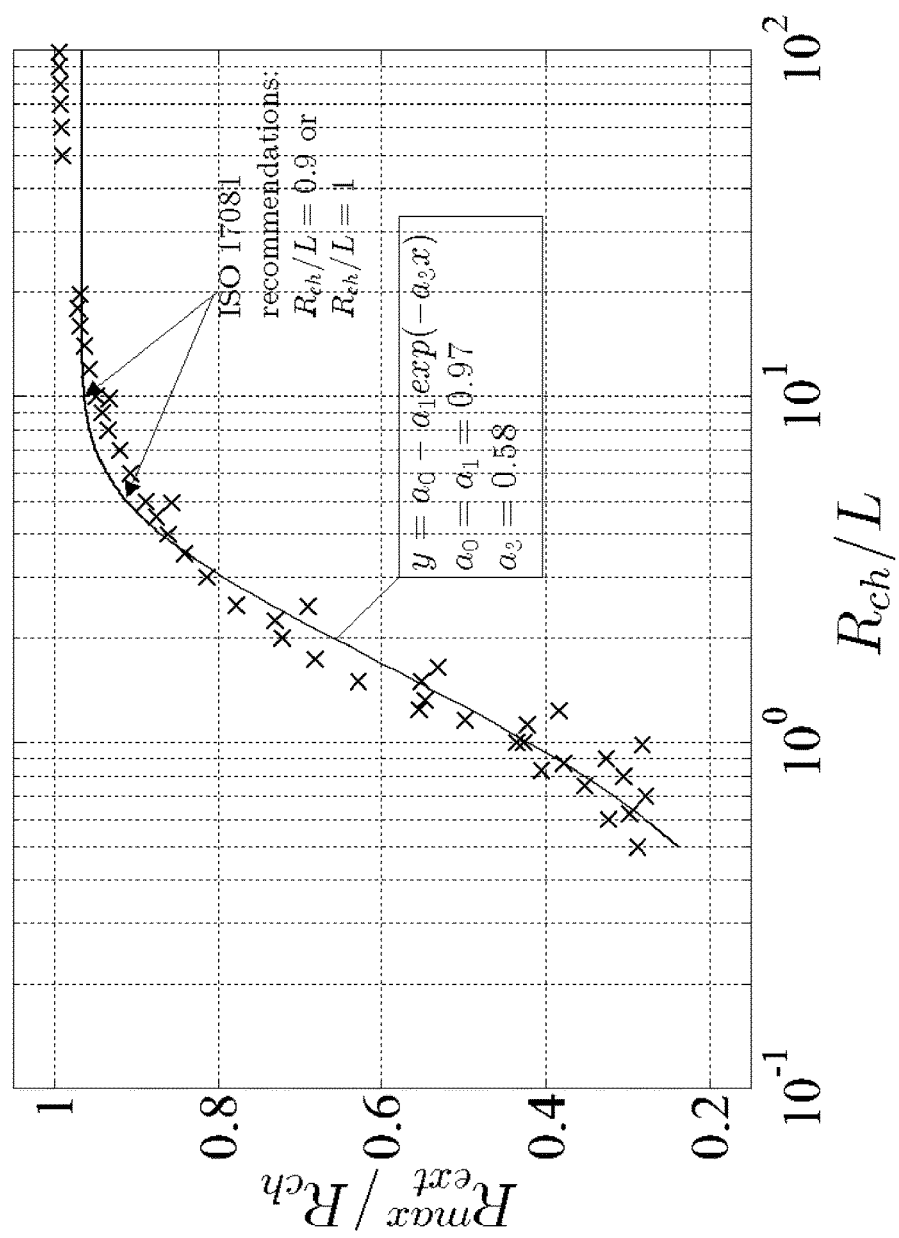
FIG. 5 is a graph illustrating the ratio of the maximum allowable extraction surface radius to the charging surface radius ($R_{ext}^{max}/R_{ch}$), as function of the ratio of hydrogen charging surface radius to the specimen thickness ($R_{ch}/L$) in accordance with one or more embodiments of the present application.

Test specimen should be manufactured to dimensions that fairly represent the actual sour service corroding equipment of interest (e.g., pipelines or pressure vessels). The importance of the dimensions of the test specimen is demonstrated in a recent published paper by Traidia et al. 2015 (Traidia, A. M. El-Sherik, and H. Attar (2015) Recommended Specimen Dimensions and Boundary Conditions for Measurement of Hydrogen Permeation in Thick Carbon Steel Plates. *Corrosion: May* 2015, Vol. 71, No. 5, pp. 585-597.), which is herein incorporated by reference. As discussed in Traidia et al., for a given ratio of hydrogen charging/corrosion surface radius ($R_{ch}$) to specimen thickness (L), the radius of the extraction surface ($R_{ext}$) is limited to an upper value ($R_{ext}^{max}$), which is lower than the charging surface radius (see FIGS. 4 and 5). In general, the test specimen should be manufactured such that the dimensions (e.g., radius) of the surface that is exposed to test solution is maximized and the radius of the extraction surface ($R_{ext}$) is minimized.

In at least one embodiment, after machining the test specimen to a particular size, both sides of the test specimen can be grinded, and then polished to 320 GRIT using a standard polishing machine. Afterwards, the test specimen can be cleaned with reverse osmosis or distilled water, rinsed with acetone and placed into an oven that is stable at a minimum of about 75° C. for approximately one hour. The test specimen can then be placed in a proper desiccator to cool. After complete cooling, the test specimen can be mounted and properly clamped to the specimen port on the test cell. In certain embodiments, an o-ring can be installed in the space between the test cell and the clamps to ensure complete sealing.

Optionally, in at least one implementation, the test cell 112 can also comprise an electrical heating belt (not shown) that wraps around the outside of the test cell 112. The heating belt can be used to perform test runs at an elevated temperature. The temperature within the test cell 112 with the use of the heating belt can vary based on the power of the heating belt, as well as the thermal diffusivity and thickness of the test cell wall. For example, in an embodiment in which the test cell is composed of PVDF and has a wall thickness of about 50 mm, a maximum temperature of about 70° C. and a maximum test pressure of about 45 psig at the inner wall of the test cell can be achieved.

As stated above, the test cell 112 can comprise one or more specimen ports 208. A schematic of the specimen port 208 and its components in accordance with one or more embodiments is shown in FIG. 6. As discussed above, specimen port 208 comprises an ultrasonic transducer 212, which is fixed (e.g., via screws) to the wedge 210. In one or more implementations, the ultrasonic transducer can be a high frequency, linear phased array transducer. The ultrasonic transducer 212 is used to monitor the initiation and growth rate of HIC in the test specimen 216. The ultrasonic transducer ("transducer") 212 can provide accurate three-dimensional maps of the HIC damage to the test specimen 216 at specified time intervals.

In conventional methods in which the ultrasonic transducer is separate from the test cell, providing an accurate three-dimensional map of HIC damage to a test specimen in laboratory environment can be challenging due to: 1) the small size of the test specimen to be scanned, 2) the limited space available in the test cell to perform the scan, and 3) the orientation of the test specimen with respect to the gravity direction. As such, the ultrasonic transducer 212 of the present application is integrated into the specimen port 208, which is an integral part of the test cell itself. As shown in FIG. 6, by being integrated into the specimen port 208, the ultrasonic transducer 212 can more easily manage any orientation of the test specimen with respect to the gravity direction. In particular, the positioning of the ultrasonic transducer 212 on the specimen port 208 results in the beam ultrasonic transducer 212 being perpendicular to plane of the HIC defects in the test specimen 216, regardless of orientation of the test specimen 216.

In one or more embodiments, the ultrasonic transducer 212 can be acoustically coupled to the wedge 210, which maintains contact with the test specimen 216 via the clamps 214. In particular, in one or more embodiments (as shown in FIG. 6), a side hole 220 can be made in one of the clamps 214 to allow for the injection of acoustic coupling (e.g., gel, oil, or water) between the wedge 210 and the scanning surface of the test specimen 216. The side hole 220 also allows for hydrogen gas that recombines at the outer surface of the test specimen to be released, thereby preventing build up and loss of acoustic contact between the wedge and the test specimen. In at least one embodiment, the wedge 210 can be comprised of plastic, such as a crosslinked polystyrene plastic (e.g., Rexolite), and acts as a delay line such that only a small amount of coupling fluid is required. This greatly reduces the risk of fluid leakage as well as the need have an additional fluid pumping system.

With continued reference to FIG. 6, the specimen port 208 is designed to have the wedge 210 maintain contact with the test specimen 216, while still allowing for the rotation of the wedge 210 with respect to the axis of the test specimen 216. More specifically, as shown in FIG. 6, the ultrasonic transducer 212 is attached to the wedge 210, but only covers half of the wedge surface. As such, the transducer 212 can continuously scan along the radial direction of the wedge 210 (and the radial direction of the test specimen 216), which allows the transducer 212 to create a map of the cross-section of the half of the test specimen 216 that is located directly below the transducer 212. Further, by rotating the wedge 210 around the vertical axis of the test specimen 216 (360° rotation), the transducer 212 also performs a full rotation around the vertical axis of the test specimen 216, thereby creating a full mapping of the entire test specimen. More specifically, by performing a full rotation of the transducer 212 around the vertical axis of the test specimen 216, and encoding the angular position (θ) of the transducer 212, a full mapping of the test specimen 216 can be achieved. Further, the proper positioning of the transducer 212 on top of the wedge 210 ensures full scanning of the test specimen 216 and prevents any overlap of scans near the axis of rotation that may result during the rotation of the transducer 212.

As mentioned above, in one or more embodiments, the angular position (θ) of the transducer is encoded to ensure a full mapping of the test specimen is achieved. The angular position (θ) of the transducer can be encoded in any number of ways known by those having ordinary skill in the art. In one or more implementations, the angular position (θ) of the transducer is encoded by using an encoder (e.g., wheel encoder) connected to the transducer and fixed to the specimen clamp such that there is permanent contact between the encoder and the wedge. In one or more implementations, a spring can be used to ensure continuous contact between the encoder and the wedge.

An example of an encoded wheel and its attachment to the transducer and the wedge is shown at FIG. 7A. As shown in FIG. 7A, assuming that there is no sliding between the wedge and the wheel encoder 502 (e.g., via a spring), a rotation of the wedge by an angle θ generates an equivalent linear displacement of the wheel encoder of $D_w \theta/2$, wherein $D_w$ is the external diameter of the wedge. The rotation of the wedge 210 triggers the transducer 212 and, therefore, results in the mapping of the test specimen 216. FIG. 7B shows an exemplary C-SCAN display of raw data obtained by the rotation of the transducer. It should be noted that the raw C-SCAN cannot be readily used for mapping purposes as it cannot be interpreted in the common way (i.e., using a Cartesian x-y plane). In fact, the raw C-SCAN has to be interpreted as a map of defects in the ($D_w \theta/2$, r) coordinate system, which is a slightly modified version of the common cylindrical coordinate system (θ, r). As such, in one or more implementations, an additional step of data processing can be needed to analyze the raw data and transpose the measurements into a Cartesian x-y plane system. In one or more embodiments, this data processing step can be accomplished using any number of software applications, such as MATLAB.

In alternative embodiments, the encoder can be other type of encoder, such as an optical encoder fixed to the wedge to encode the rotation. Further, in embodiments in which a motor is used to rotate the ultrasonic transducer, the motor itself can include an encoder to log the circumferential position of the wedge.

As discussed above, in one or more embodiments, the ultrasonic transducer 212 is positioned on top of the wedge 210. This positioning of the ultrasonic transducer 212 ensures full scanning of the test specimen and prevents any scan overlap near the axis of rotation that may result during the rotation of the transducer. For the purpose of ensuring full scanning and preventing scan overlap in these embodiments, three main factors can be taken into account.

Figure 8:
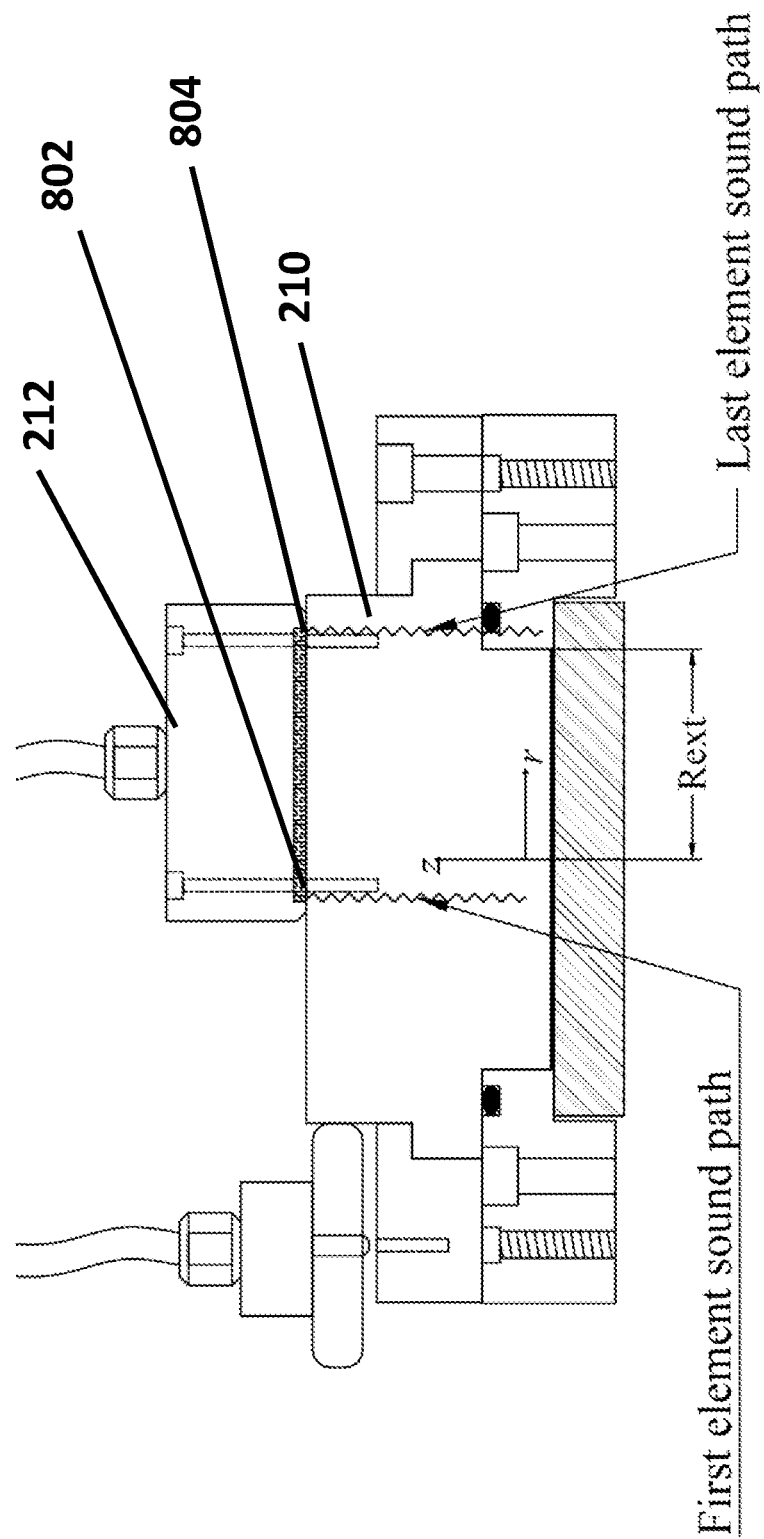
FIG. 8 is a schematic of the sound path for the first and last firing elements of the ultrasonic transducer in accordance with one or more embodiments of the present application.

First, the ultrasonic transducer length must be at least equal to the radius of the hydrogen extraction surface ($R_{ext}$). In a preferred embodiment, the ultrasonic transducer length can be slightly larger than $R_{ext}$, such as $1.2 \times R_{ext}$. Second, the wedge has to be designed such that the ultrasonic transducer is fixed on only half of the wedge with the first few firing elements ("elements") of the ultrasonic transducer firing in the region where r<0, and the last few elements of the transducer firing in the region where $r > R_{ext}$. This results in the region of interest ($0 < r < R_{ext}$) being fully scanned. FIG. 8 illustrates the sound paths for the first (802) and last elements (804) of the transducer, in accordance with at least one embodiment. Third, in order to prevent scan overlapping in the region where r<0, the transducer elements firing in that region can be de-activated such that the first beam (focal law) of the transducer hits the specimen at its center. In other words, in one or more embodiments, the transducer can be calibrated prior to a test run to determine which transducer elements need to be de-activated to prevent overlap. By deactivating these select transducer elements, the scanning of the area located at r<0 is prevented.

Figure 9:
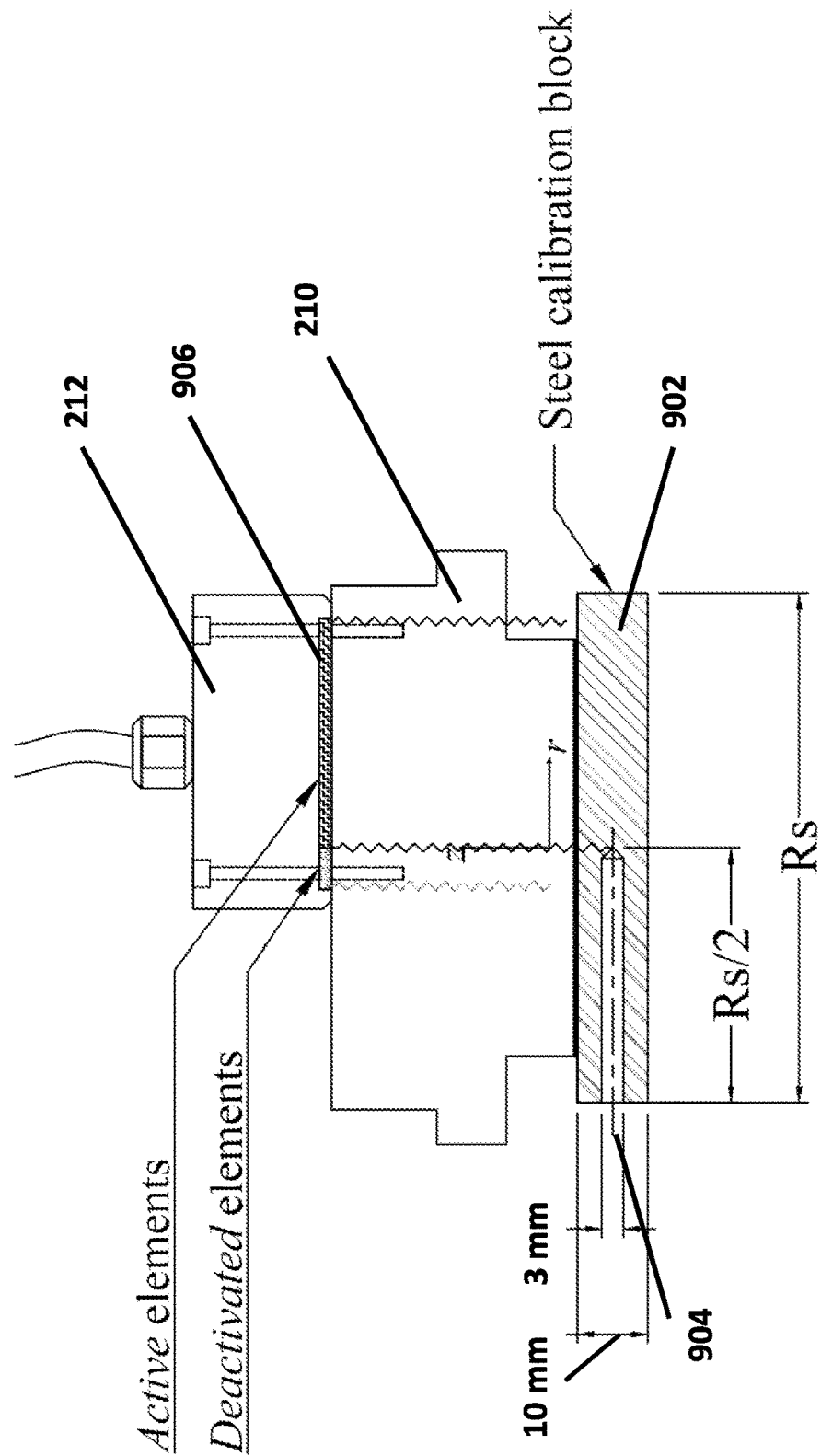
FIG. 9 is an illustration of a technique used to determine the first firing element of the transducer to prevent scan overlapping in the region r<0 using a calibration block, in accordance with one or more embodiments of the present application.

In one or more embodiments, in order to determine which transducer elements should be deactivated, a calibration block can be positioned in the specimen port to calibrate the transducer prior to a test run. As shown in FIG. 9, a calibration block 902 can be positioned in the specimen port (where the test specimen would be positioned) adjacent to the wedge 210. In this embodiment, the calibration block 902 is made of steel and has a thickness of 10 mm; however, other embodiments can have a calibration block 902 of varying thicknesses. Further, a side hole 904 (3 mm in diameter in this embodiment) is drilled radially into the proximal end of the calibration block 902 a distance of Rs/2, where "Rs" represents the radius of the specimen, stopping at the center of the block. In one or more implementations, the diameter of the side hole 904 should exceed at least the sensitivity of the transducer. After drilling the side hole 904 and positioning the calibration block 902 in the specimen port, the transducer elements 906 can then be tested on the calibration block and its settings (e.g., aperture, focal law, first active element, last active elements) fine-tuned or calibrated such that only the transducer elements between the center of the block (i.e., end of the side hole) and the distal end of the calibration block are turned on. Once calibration is complete, the calibration block 902 can be replaced with the test specimen in the specimen port. As such, during the subsequent test run, only the area between the center of the test specimen and the distal end of the test specimen are scanned.

In alternative embodiments, at least one specimen port of the test cell can be used to monitor the hydrogen permeation rate (i.e., the flux of the hydrogen through the specimen thickness). More specifically, to monitor the hydrogen permeation rate, a different specimen clamp (as compared with the specimen clamp for monitoring HIC) allows for the collection of the volume of hydrogen gas that diffuses through the specimen during the test duration.

An exemplary embodiment featuring a hydrogen permeation specimen clamp is shown at FIG. 10. FIG. 10 displays an embodiment featuring two specimen ports: one featuring a specimen clamp 214 for facilitating the measurement of HIC initiation and growth rate in a specimen, and a hydrogen permeation (HP) specimen clamp 1014 for facilitating the determination of the hydrogen permeation rate through a specimen. As with the specimen clamp 214, the HP specimen clamp 1014 holds the specimen 216 in place within the specimen port. The HP specimen clamp 1014 comprises: a drilled hole 1010 through the center of the clamp 1014, as well as a connector 1012 for attaching to the hole 1010 on one end and connecting to an eudiometer 1016 via tubing 1018 on the other end. In this embodiment, the volume of hydrogen gas that diffuses through the test specimen held in the HP specimen clamp 1014 is collected on the outer facing side of the HP specimen clamp 1014 using a standard eudiometer technique known in the art. Additionally features of the HP specimen clamp 1014 are shown in FIGS. 11A-C, which provides a top view (A), a bottom view (B), and a cross-sectional view (C) of the HP specimen clamp 1014. As shown in FIGS. 11A-C, the HP specimen clamp 1014 can comprise two or more drilled holes 1020 around the perimeter of the clamp 1014 for holding the clamp 1014 to the specimen port (e.g., via screws). In this exemplary embodiment shown in FIGS. 11A-C, there are 8 drilled holes 1020 around the perimeter of the clamp 1014.

As such, in an embodiment (such as FIG. 10) in which at least one specimen in held in a HP specimen clamp 1014 and at least one specimen is held in a specimen clamp 214, the system can measure, HIC growth rate, corrosion rate and hydrogen permeation rate in a single run. Further, in these embodiments, the test run can be used to determine a correlation between the measured HIC growth rate and hydrogen permeation rate for a particular type of test specimen because all test specimens are simultaneously exposed to the same test solution. Additionally, at the end of each test run, the weight of the different test specimens can be measured compared with the initial weight of each test specimen (which shall be measured before clamping the specimens to the test cell), which allows the operator of the system to determine the corrosion rate of each test specimen. As such, in embodiments including at least one an HP clamp 1014 and at least one specimen clamp 214, the system of the present application can measure HIC growth rate, hydrogen permeation rate, and corrosion rate in a single test run. As mentioned above, once the one or more test specimens are in the specimen port(s) and the test solution has been successfully transferred to the test cell (to the semi-open fluid vessel 202 of the test cell), the one or more test specimens can be monitored for HIC defects in real time. The ultrasonic transducer 212 can monitor development and growth of HIC defects by scanning the test specimen(s) at different time points during the test run. More specifically, the ultrasonic transducer 212 can monitor the HIC defects on the test specimen by rotating (with the wedge 210) from 0 to 360 degrees with respect to the axis of the test specimen. In one or more embodiments, a motor can be fixed onto the wedge 210 to automate the rotation of the wedge (and, as such, the ultrasonic transducer) at a specific frequency. In at least one embodiment, the motor can automate the rotation of ultrasonic transducer itself, while the wedge 210 remains stationary. In at least one embodiment, the wedge 210 and/or the ultrasonic transducer can be rotated manually.

As mentioned previously, the test cell holder can maintain the test cell 112 at neutral position (0 degrees with respect to gravity direct) or can rotate and lock the test cell 112 at +45 degrees and −45 degrees with respect to the gravity direction. Rotation of the test cell holder (via the rotating test cell holder) allows for the testing of the test specimens at different positions with respect to gravity, thereby closely mimicking the conditions of different portions of a pipe. Indeed, different portions of the pipe (e.g., 3 o'clock to 9 o'clock [+45 degrees to −45 degrees with respect to the gravity direction]) can experience different corrosion rates and therefore different HIC growth rates. This is due to the local concentration of water in the test solution, which is affected by the gravity direction. In particular, water tends to settle at around the 6 o'clock position (0 degrees with respect to the gravity direction), which makes this region the most critical for corrosion and HIC growth.

For example, FIGS. 12A-C shows a schematic of the different orientations of the test cell and test specimens in accordance with one or more embodiments of the present application. In this embodiment, the test cell comprises two test specimens and, as such, can allow for a test specimen to be located at 5 different positions with respect to gravity. More specifically, when the test cell 112 is in a neutral position (00 rotation with respect to gravity), one test specimen is located at a "4:30" clock position, and the other test specimen is located at a "7:30" clock position (FIG. 12A). However, in FIG. 12B, when the test cell 112 is rotated +45° from neutral (45° in a clockwise direction), one test specimen is located at a "9 o'clock" position and the other test specimen is located at a "6 o'clock" position. Similarly, in FIG. 12C, when the test cell 112 is rotated −45° from neutral (45° in a counterclockwise direction), one test specimen is located at a "3 o'clock" position and the other test specimen is located at a "6 o'clock" position. The rotation of the test cell allows for the testing of specimens that closely simulate different angles of a pipe in a sour environment. As such, the present invention will allow for greater predictive accuracy of HIC growth on an actual pipeline compared with conventional methods, regardless of what portion of the pipe (e.g., top, bottom, side) has developed a crack. It should be noted that having multiple test specimens in one test cell allows for comparison of the test specimens and thus greater confidence in the accuracy of the results.

Regardless of which position(s) the test specimen(s) are in, only one surface of each test specimen is exposed to the saturated test solution, thus mimicking the conditions of a sour gas service line. The test duration for the one or more test specimens can vary (e.g., the test duration could be a matter of minutes or several weeks) depending on the thickness of the test specimen, and the susceptibility of the test specimen to the corrosive test solution. Additionally, the test specimen(s) can be scanned using the ultrasonic transducer at several different points during the test period in order to measure the crack growth over time and the crack size at different time points. In one or more embodiments, the test specimen(s) can be scanned frequently at the beginning of the test period to capture the initiation of multiple site HICs, which tend to grow faster at the beginning of the test period. Additionally, the time between scans can be increased (i.e., the frequency of inspection can be reduced) at the latter stages of the test period, as the HIC growth rate tends to decrease at this time.

Referring again to FIG. 1, after the test run ends, the main valve of container 104 ($H_2S$ container) is closed. The experimenter can then close valve V19 and regulator R4 once the pressure of the system 100 has dropped to 0 (as shown in gauge G9). The system 100 can then be purge with $N_2$ gas for a minimum of 24 hours before opening the test cell. The $N_2$ purging is accomplished by fully opening valves V4 and V8, and regulators V7 and V9. In parallel, valve V15 is slowly opened and the pressure in gauge G9 is not increase over 15 psig. After purging the system 100 with $N_2$ for 24 hours, valve V13 can be closed in order to open the test cell to dispose of the test solution and perform further analysis on the test specimens (e.g., metallography). It should also be noted that, in the case of an emergency during a test run, the experimentalist can immediately shut off the main valve of container 104 (the $H_2S$ container), and open valves V3, V12, and V13 (vent).

As mentioned above and as shown in FIG. 1, in one or more embodiments the system 100 can also comprises one or more scrubber tanks 116. In one or more implementations, the scrubber tank(s) 116 contain a basic (i.e., high pH) scrubber solution, such as sodium hydroxide or potassium hydroxide, where the scrubber solution is used to "scavenge" any $H_2S$ gas flowing out of the test cell. In preferred embodiments, the system includes at least two scrubber tanks. In these embodiments, only one scrubber tank is used at a time during a test run. In particular (with continued reference to FIG. 1), when the test is running, only one scrubber tank (e.g., S1) is used to dissolve/scavenge the $H_2S$ exiting the system. When the color of the scrubber solution contained in the current scrubber tank (S1) becomes "yellowish," the scrubber solution is being saturated with $H_2S$ and the operator must redirect the flow of gas towards a second (back-up) tank (S2) using valve V22. Afterwards, the operator may empty the saturated scrubber tank (S1) and refill it with a fresh scrubber solution. In one or more implementations, the one or more scrubber tanks are transparent, allowing the operator to more easily determine when the scrubber solution becomes "yellowish" (i.e., saturated with $H_2S$).

In one or more implementations, the system 100 can also include one or more trap cylinders 118. The purpose of the trap cylinder(s) 118 is to verify that the gas is flowing properly inside the test cell. The trap cylinder(s) 118 are partially filled with water and the gas tubes are immersed inside these trap cylinders. During normal operation of the system 100, gas is bubbling inside the cylinders, which provides verification of proper gas flow in the system. However, if the bubbling stops, that signals to the operator that there is a blockage somewhere ahead of the traps cylinder(s) 118 and the test must be stopped. In one or more implementations, the trap cylinder(s) 118 are transparent to allow the operator to more easily determine if there is proper gas flow in the system.

EXAMPLE

The following example is provided to further illustrate embodiments of the present invention, but it should not be construed as limiting the scope of the present invention.

Example 1

Two test specimens were monitored for HIC and hydrogen permeation. The test was conducted using a test cell designed to operate at a maximum temperature of 70° C. and a maximum pressure of 45 psig. The test cell comprised two specimen ports: a first specimen port (connected to a eudiometer) for measuring hydrogen permeation of a test specimen (specimen 1) and a second port for monitoring the development of HIC in a test specimen (specimen 2) using a rotating ultrasonic transducer. The rotating ultrasonic transducer allowed for the detection and scanning of hydrogen-induced cracks at a minimum size of 0.1 mm.

Both test specimens were exposed to the test solution in the test cell for a predetermined amount of time, such as about 180 minutes (3 hours). The test cell was oriented at 0 degrees with respect to the gravity direction for the duration of the test. At select time points throughout the test run, the permeation rate measurements are taken. At the end of the test run (e.g., about 180 minutes in one exemplary test run), specimen 2 was scanned using the rotating ultrasonic transducer to produce a map of the final HIC damage state.

Figure 13:
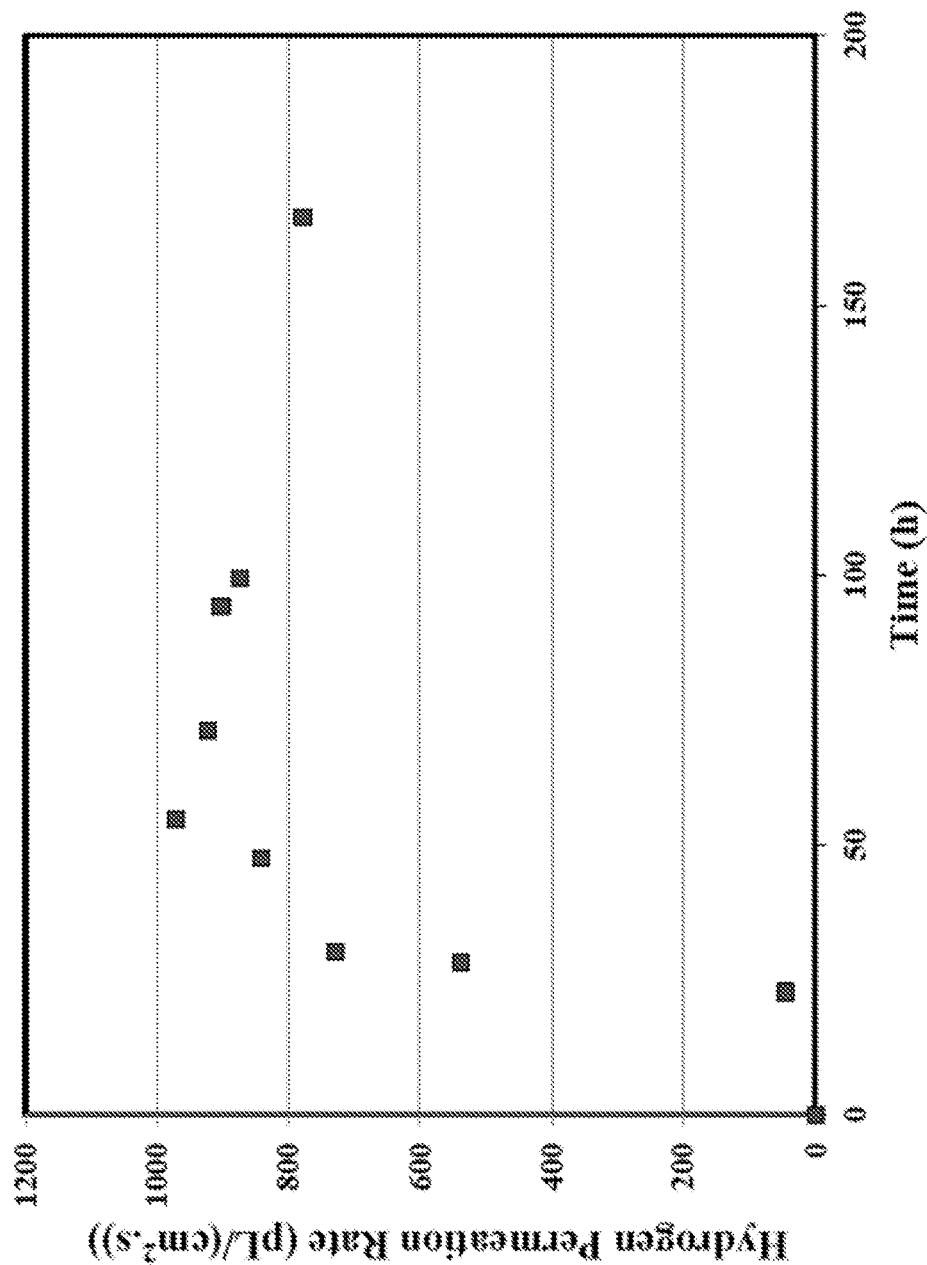
FIG. 13 is a graph of the hydrogen permeation rate of a test specimen over the test period of Example 1, in accordance with one or more embodiments of the present application.

The results of the hydrogen permeation rate measurements during the test are shown at FIG. 13. As shown by the graph, the hydrogen permeation rate rose drastically within the first 60 minutes of exposure to the test solution to close to 1000 $pL/cm^2 \cdot s$. The hydrogen permeation rate slightly decreased for the remainder of the test duration, finishing at near 800 $pL/cm^2 \cdot s$.

Figure 14B:
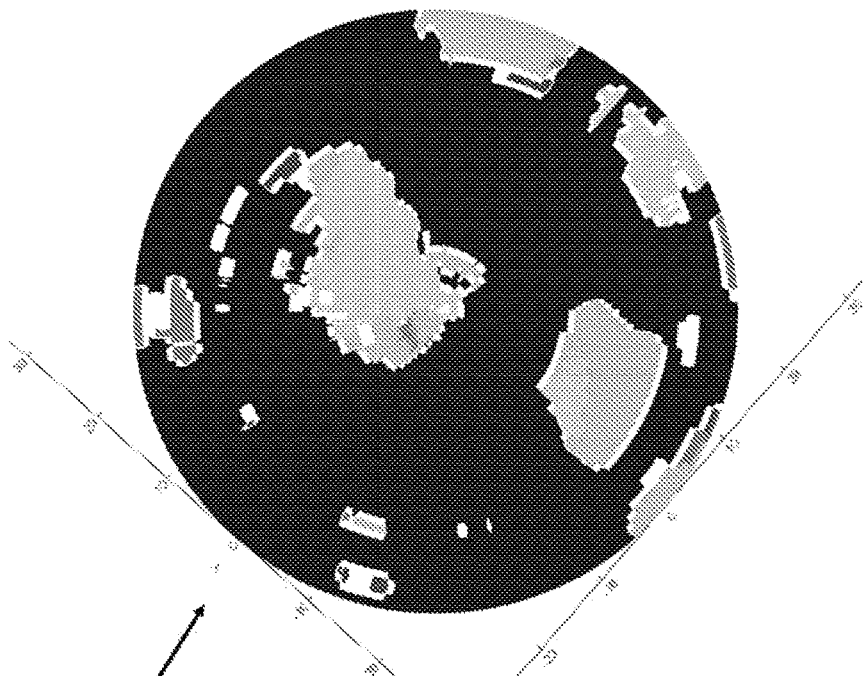
FIGS. 14A-B are scans of the test specimen using an immersion ultrasonic scanner (14A) and a rotating ultrasonic scanner (14B) at the end of the test period of Example 1, in accordance with one or more embodiments of the present application.
Figure 14A:
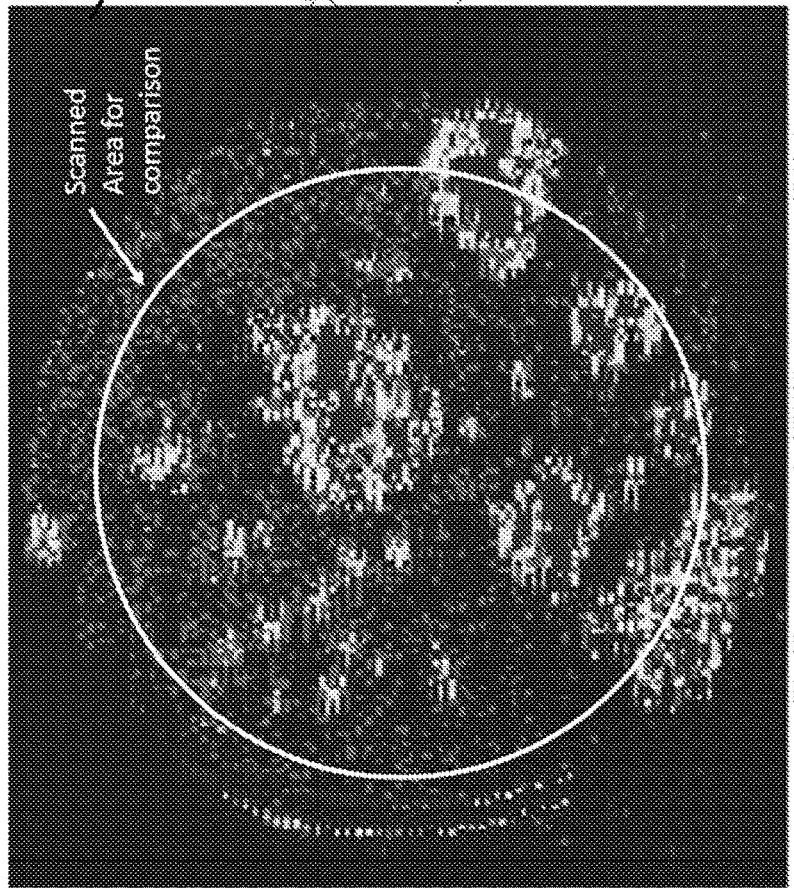

At the end of the test duration, specimen 2 was removed from the test cell and placed into a water bath to get a second map of the final HIC damage state using a high frequency immersion ultrasonic transducer testing. The map of HIC damage created using the immersion ultrasonic transducer testing (FIG. 14A) was then compared with the map created by the rotating ultrasonic transducer (FIG. 14B). This comparison revealed excellent agreement between the two maps, thereby confirming the results shown via the rotating ultrasonic transducer mapping.

The terminology used in the above description is for the purpose of describing particular embodiments only and is not intended to be limiting of the invention. As used herein, the singular forms "a", "an" and "the" are intended to include the plural forms as well, unless the context clearly indicates otherwise. Further, it will be understood that the terms "including," "comprising," "having," "containing," "involving," and variations thereof herein, when used in this specification, specify the presence of stated features, integers, steps, operations, elements, and/or components, but do not preclude the presence or addition of one or more other features, integers, steps, operations, elements, components, and/or groups thereof.

It should also be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

While the present invention has been described above using specific embodiments, there are many variations and modifications that will be apparent to those having ordinary skill in the art. As such, the described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A system for monitoring hydrogen-induced cracking in a laboratory environment, comprising:
a source of sour gas;
a test solution tank comprising a test solution and into which the sour gas is introduced such that the test solution becomes saturated with the sour gas;
a test cell defining a semi-open fluid vessel, the fluid vessel being in fluid communication with the test solution tank such that the fluid vessel receives the saturated test solution;
a test cell holder configured to rotate the test cell;
at least one specimen port operatively connected to the fluid vessel and configured to hold a test specimen such that one surface of each test specimen is exposed to the saturated test solution; and
an ultrasonic transducer operatively connected to the at least one specimen port and configured to rotate to scan HIC defects of the test specimen.

2. The system of claim 1, wherein the test cell holder is configured to rotate the test cell about −45 degrees relative to the direction of gravity and lock the test cell at that position for a test duration.

3. The system of claim 1, wherein the test cell holder is configured to rotate the test cell about +45 degrees relative to the direction of gravity and lock test cell at that position for a test duration.

4. The system of claim 1, wherein the ultrasonic transducer is configured to rotate with respect to the symmetry axis of the test specimen.

5. The system of claim 1, wherein each specimen port comprises a wedge on top of which the ultrasonic transducer is attached, and wherein the wedge is configured to rotate with respect to the symmetry axis of the test specimen resulting in the rotation of the ultrasonic transducer.

6. The system of claim 5, wherein the ultrasonic transducer covers half of the top surface of the wedge.

7. The system of claim 6, wherein the wedge is rotated manually.

8. The system of claim 6, wherein the wedge is operatively connected to a motor such that the motor automates the rotation of the wedge and the ultrasonic transducer.

9. The system of claim 1, wherein the system comprises at least two specimen ports.

10. The system of claim 9, wherein the system comprises at least one specimen port configured to connect to a eudiometer device for measuring the hydrogen permeation rate through the test specimen.

11. The system of claim 1, wherein the at least one test specimen is comprised of a metal that is susceptible to hydrogen-induced cracking.

12. The system claim 11, wherein each test specimen is comprised of steel.

13. The system of claim 1, wherein the system further comprises a fluid conduit for transferring the saturated test solution from the test solution tank to the fluid vessel of the test cell, the fluid conduit being positioned such that it terminates in front of the each specimen port within the fluid vessel of the test cell.

14. The system of claim 13, wherein the system further comprises one or more screens attached to the end of fluid conduit 110 that terminates within the fluid vessel of the test cell, the screens being configured to agitate the test solution exposed to the test specimen.

15. The system of claim 1, further comprising an encoder operatively connected to the ultrasonic transducer and fixed to the specimen clamp, wherein the encoder is configured to be linearly displaced as the wedge rotates, resulting in a full scan of the test specimen.

16. The system of claim 15, wherein the encoder is a wheel encoder.

17. The system of claim 16, wherein the encoder is an optical encoder.

* * * * *